United States Patent [19]
Harwell et al.

[11] Patent Number: 6,032,544
[45] Date of Patent: Mar. 7, 2000

[54] AUTOMATED PARTICLE MONITOR FOR A THIN FILM PROCESS

[75] Inventors: Cheryl Diane Harwell, Atascosa; Ray Rudi Rayniak, San Antonio, both of Tex.

[73] Assignees: Sony Corporation, Tokyo, Japan; Sony Electronics Inc., Park Ridge, N.J.

[21] Appl. No.: 09/325,267

[22] Filed: Jun. 3, 1999

Related U.S. Application Data

[62] Division of application No. 08/923,700, Sep. 4, 1997, Pat. No. 5,942,672.

[51] Int. Cl.⁷ .................................................. G01N 1/00
[52] U.S. Cl. ........................................................ 73/865.5
[58] Field of Search ................................... 73/1.01, 1.02, 73/1.06, 1.07, 865.5

*Primary Examiner*—Robert Raevis
*Attorney, Agent, or Firm*—Wood, Herron & Evans, LLP

[57] ABSTRACT

A method of calibrating a particle monitor prior to applying DC power to a cathode in the processing chamber by first, initiating a flow of gas to the processing chamber. Next, the operation of the particle monitor is initiated to obtain a particle count within the flow of gas in the processing chamber. If the particle monitor detects a particle count in excess of a minimum value, the operation of the particle monitor is adjusted to reduce the particle count to the minimum value. During production, the particle monitor count is initiated by a particle monitor control only after the particle monitor control detects an occurrence of both a first signal generated in response to initiating a flow of gas to the processing chamber and, a second signal generated in response to the application of power to a cathode within the processing chamber.

11 Claims, 2 Drawing Sheets

AUTOMATED PARTICLE MONITOR FOR A THIN FILM PROCESS

This application is a Divisional of Ser. No. 08/923,700, filed Sep. 4, 1997, now U.S. Pat. No. 5,942,672.

FIELD OF THE INVENTION

This invention relates to sputter processing and more particularly, to the use of a particle sensor in the sputtering process.

BACKGROUND OF THE INVENTION

In the manufacture of semiconductors, one or more coating or etching processes may be used. One of such processes is a physical vapor deposition ("PVD") sputter coating process. In a PVD process, a heavy gas, for example, argon, is ionized in a vacuum chamber. The argon ions impact a target and sputter off target material atoms, for example, aluminum, that are, in turn, deposited on a substrate or wafer. Thereafter, an etching process is used to leave a predetermined pattern of the material on the wafer. In other PVD applications, the target is titanium, and one or more reactive gases, for example, nitrogen and oxygen, are bled into the chamber to form either titanium nitride or titanium oxynitride.

During the PVD process, the target material being sputtered is not only deposited on the wafer, but is also deposited on other surfaces and shields within the vacuum chamber. Over a number of sputtering cycles, the thickness of the sputtered material on the shields and other surfaces within the vacuum chamber continuously increases. Further, with each sputtering cycle, the chamber and the components therein experience a heating and cooling temperature cycle. After a period of time, as the coating of sputtered material thickens on the shields, it has a tendency with successive temperature cycles to flake off of the shields in the form of small particles that range in size from approximately 0.1 microns to approximately several microns. Once in the environment of the vacuum chamber, it is highly probably that a particle will be deposited on a the substrate being processed. Normally, the sputtering material is a conductor; and therefore, if the particle is deposited across terminals of a device or across conductive paths on the substrate, the resultant short circuit is substantially thicker than the coating. Therefore, the subsequent etching process to remove the coating will not remove all of the particle; and the remaining unetched particle may create a short circuit which make an associated device on the wafer unuseable. Therefore, those larger particles which flake off of shields and surfaces in the processing chamber have an adverse impact on and reduce the yield of the completed wafer devices.

Process yields can be improved if the shields and other surfaces in the processing chamber are cleaned prior to the time when excessive particles begin to flake therefrom. The cleaning of chamber surfaces and the removal and replacement of the shields is a time-consuming and expensive process during which the sputtering chamber is out of production. Therefore, the cleaning process is preferably conducted only when necessary. However, postponing the cleaning process to the point where particles begin flaking from the coated surfaces, thereby reducing yields, is more costly than the cleaning process. Ideally, the processing chamber should remain in production right up to the time immediately prior to particle flaking.

In the past, the processing time of the chamber 22 was measured in kilowatt hours; and based on experience, the chamber was scheduled to be cleaned after the passage of a predetermined number of processing kilowatt hours. However, predicting the optimum time to clean a processing chamber by tracking the kilowatt hours of processing does not provide the optimum production processing time between cleaning procedures.

To improve the prediction of when maintenance and cleaning should be performed, a particle monitor can be used. One such monitor is an external laser based monitor capable of detecting very small particles. However, the cost of such a monitor makes its application to all processing chambers impractical. Another, less expensive, in-situ monitor can also be used, for example, a particle sensor model No. 20SD, commercially available from High Yield Technology of San Jose, Calif. The in-situ particle monitor includes a particle sensor control connected to an electronic laser probe that is located in the vacuum chamber. With such a particle sensor, a laser beam illuminates the plasma of gas ions and provides a count of particles within the plasma that are within a range of particle sizes, for example, from approximately 0.3 microns to approximately 5.0 microns. The microns are counted over a predetermined sample time period, or sample window. The total number of particles counted during a sample window is compared to a set point representing a threshold particle count value; and if the count exceeds the threshold value, an alarm is provided by the particle sensor control. The set point value is empirically determined to provide the most effective time at which to initiate a maintenance and cleaning of the processing chamber.

There are two disadvantages in the current application of the in-situ monitor. First, the particle monitor is enabled by a control signal derived from the application of power to the target cathode of the processing chamber. When power is applied to the target, the plasma of ionized gas provides significant interference and noise to the in-situ particle monitor that masks particles that otherwise could be counted. The net result is that the monitor is not counting all of the particles that it is capable of accurately discriminating. Therefore, there are more particles in the processing chamber than indicated by the particle monitor, and those undetected particles have a substantially adverse impact on yields. Second, there are certain times when power is applied to the target, but a production wafer is not located in the processing chamber. Therefore, the in-situ particle monitor is operating and collecting data during time periods when production is not occurring. Not only does such operation waste valuable memory space in the particle sensor control but any particle alarms that occur during nonproduction periods are a distraction to personnel.

Consequently, there is a need for an improved system for controlling the operation of a particle sensor during the coating process.

SUMMARY OF THE INVENTION

The present invention provides an improved method of using a particle monitor located in a processing chamber by providing an in-situ method of calibrating the particle monitor in the processing chamber. The in-situ calibration minimizes the adverse effects of the gas flow on the particle count and has the advantage of permitting the particle monitor to be used to more accurately predict times at which the processing chamber should be cleaned. The present invention further provides a improved method of initiating the operation of the particle monitor so that the particle monitor is only operating during production situations. Such improved method of operation has the advantage of optimizing the use of memory for storing particle counts and minimizing the distraction of particle count alarms on personnel during nonproduction periods.

According to the principles of the present invention and in accordance with the preferred embodiments, the invention provides a method of calibrating a particle monitor in a processing chamber. The calibration process is initiated prior to applying DC power to a cathode in the chamber. The process first initiates a flow of gas to the processing chamber and thereafter, initiates the operation of the particle monitor to obtain a particle count within the flow of gas in the processing chamber. If the particle monitor detects a particle count in excess of a minimum value, the operation of the particle monitor is adjusted to reduce the particle count to the minimum value. Therefore, the particle monitor is calibrated in-situ in the processing chamber to minimize the effects of the flow of the gas on the particle counting process. Hence, the in-situ calibration has an advantage of providing a more accurate particle count during a process after power is applied to the cathode.

In another embodiment of the invention, the invention provides a method of operating a particle monitor with a particle monitor control in a processing chamber. A first signal is provided to the particle monitor control in response to initiating a flow of gas to the processing chamber. A second signal is provided to the particle monitor control in response to the application of power to a cathode within the processing chamber. Thereafter, the operation of the particle monitor is initiated by the particle monitor control only after the particle monitor control detects an occurrence of both of the first and the second signals. Since a production process is always being run in the presence of the flow of gas and power being applied to the cathode, the particle count is only taken after both of those conditions have occurred. Hence, the improved method of operation has the advantage of not using particle count memory and not providing particle alarms during nonproduction periods.

These and other objects and advantages of the present invention will become more readily apparent during the following detailed description taken in conjunction with the drawings herein.

DETAILED DESCRIPTION OF THE INVENTION

Figure 1:
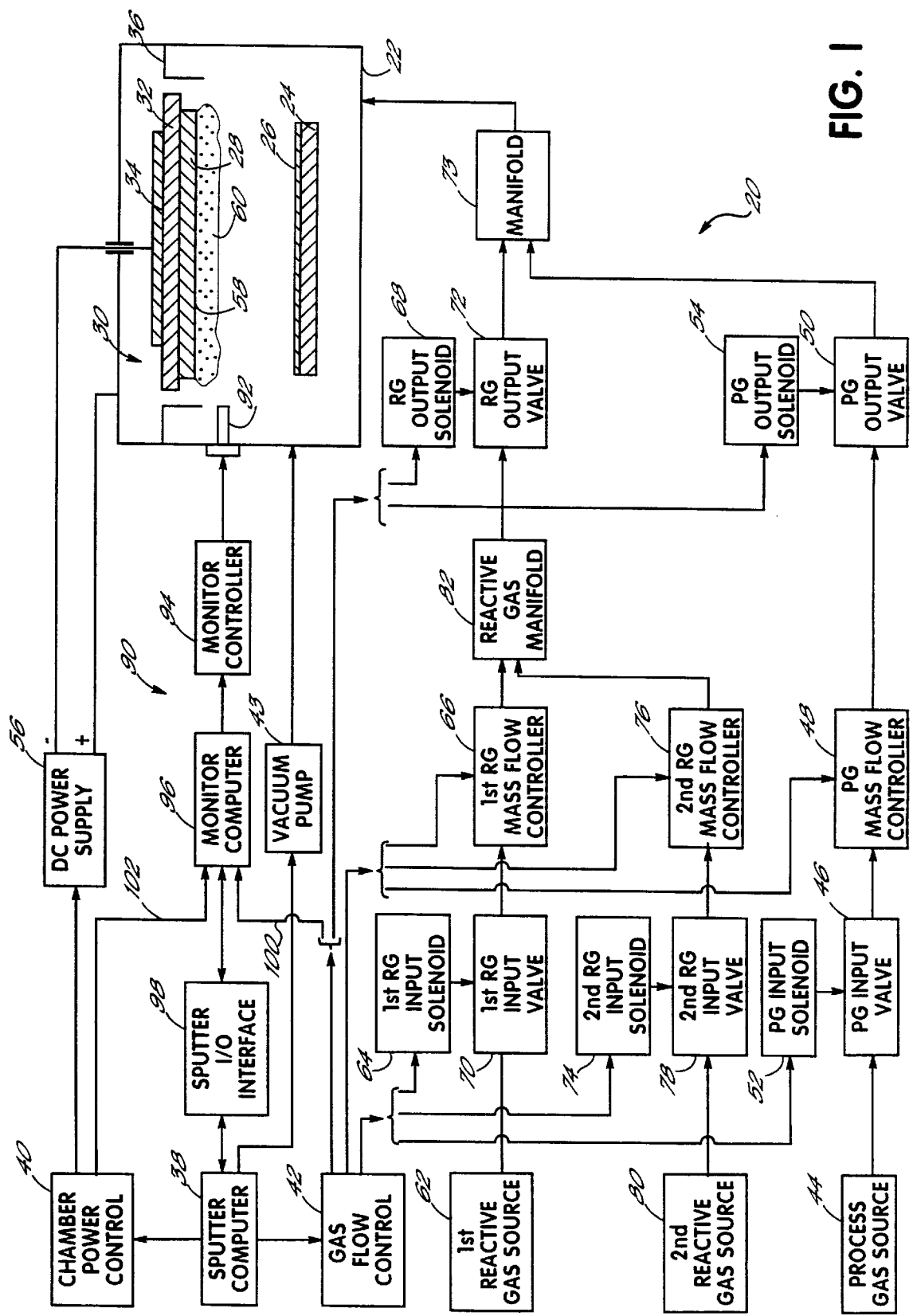
FIG. 1 is a schematic block diagram of a sputtering system including the an in-situ particle monitor in accordance with the principles of the present invention.

Referring to FIG. 1, a PVD sputter coating apparatus 20 includes a vacuum type sputter processing chamber 22 having a wafer support 24 for supporting a semiconductor wafer 26 mounted thereon. The wafer 26, when mounted on the support 24, is parallel to and faces a target 28 of sputter coating material, for example, aluminum or titanium, of the type that is to be deposited as a thin film on the wafer 26. The target 28 is part of a cathode assembly 30 that includes a target holder 32, to which the target 28 is secured. A magnet pack 34 is typically provided behind the target holder 32 on the side opposite from the wafer support 24. Shields 36, for example, a dark space shield and other shields, are located respectively, around the periphery of the target 28 and at other locations in the processing chamber 22 in a known manner. The magnet pack 34 preferably includes magnets that produce a closed magnetic tunnel that traps over the surface of the target 28 electrons given off by the cathode assembly 30 into gas within the chamber 22. The magnet pack 34 may include fixed or rotating or otherwise moving magnets which may be permanent or electromagnets in the form of any one of a number of magnetron sputtering machines known in the art.

The operation of the sputter coating apparatus 20 is normally described in a recipe tailored to a particular coating process. The recipe is entered by an operator into a sputter computer 38; and prior to any processing, the sputter computer 38 commands a vacuum pump 43 to a pump the processing chamber 22 to a vacuum in the milliTorr or submilliTorr range. Thereafter, pursuant to the recipe, the sputter computer 38 provides control signals to a chamber power control 40 and gas flow control 42 to provide the desired electrical power and gas flow to the processing chamber 22. For example, a source of process gas 44, which is typically an inert gas such as argon, is connected to the processing chamber 22 via a PG gas input valve 46, PG mass flow controller 48 and PG output valve 50. When the recipe requires the flow of argon from the process gas source 44 to the processing chamber 22, the sputter control 38 provides command signals to the gas flow control 42, which, in turn, provides control signals to a PG input solenoid 52, the PG mass flow controller 48, and PG output solenoid 54 commanding the PG input valve 46 and PG output valve 50 to open, thereby providing a flow of the argon process gas from the source 44 to the processing chamber 22. The desired flow of the process gas is determined by the PG mass flow controller 48 which is controlled by the gas flow control 42 in a known manner.

When the recipe requires the application of power to the cathode assembly 30, the sputter computer 38 commands the chamber power control 40 to turn on a DC power supply 56, which may be controlled to provide either a constant or pulsed power to the target 28. The power from the DC power supply 56 produces a negative potential on the target surface 58 of cathode assembly 30, which causes electrons to be emitted from the target surface 58. The wafer support 24 is connected to ground and functions as an anode. The electrons remain trapped over the surface 58 by the magnetic field generated by the magnet pack 34 until they strike and ionize atoms of the argon process gas that are in close proximity to the target surface 40, thereby forming a plasma 60 adjacent the target surface 58. The plasma 60 becomes a source of positive ions of argon gas that are accelerated toward and against the surface 58 to eject particles of coating material from the target 28.

In some sputter coating applications, the target 28 is made of a titanium material; and a reactive gas, for example, a nitrogen, is provided to the chamber 22 from a first reactive gas source 62. As with the argon process gas, at the appropriate times determined by the recipe, the gas flow control 42 provides command signals to a first reactive gas input solenoid 64, a first reactive gas mass flow controller 66, and a reactive gas output solenoid 68, which causes the first reactive gas input valve 70 and reactive gas output valve 72 to open. The command signal from the gas flow control 42 to the first reactive gas mass flow controller 66 establishes a desired mass flow of the first reactive gas from the gas source 62 to a manifold 73 where the nitrogen reactive gas mixes with the argon process gas, and the gas mixture flows into the processing chamber 22. In other sputter coating applications, the recipe may call for a second reactive gas, for example, oxygen to be used in combination with the nitrogen gas. In those applications, the gas flow control 42 provides command signals to the second reactive gas input solenoid 74 and second reactive gas mass flow controller 76. The command signals cause the second reactive gas input valve 78 to open and the mass flow controller 76 to regulate the flow of the second reactive gas from the second reactive gas source 80 to a reactive gas manifold 82. The nitrogen and oxygen reactive gases are mixed in the manifold 82 prior to flowing through the open RG output valve 72, mixing with the argon process gas in manifold 73 and then, flowing as a three gas mixture into the processing chamber 22.

As previously discussed, the sputter coating process not only provides a material coating on the wafer 26, but in addition, coats the shields 36 and other surfaces within the processing chamber 22. After a number of sputter coating cycles, the coating of material will accumulate on the shields 36 and other surfaces to the extent that further accumulations result in material flaking off as particles within the chamber. Those particles, if they contact the wafer 26, can potentially short circuit leads and signal paths or physically damage the leads or signal paths. To detect the presence of harmful particles, an in-situ particle monitor 90, for example, the previously described High Yield Technology particle monitor is used. The in-situ particle monitor 90 includes an electronic laser probe 92 connected to a monitor controller 94 which in turn is connected to a monitor computer 96. The probe 92 is located inside of the processing chamber 22 such that the laser light is directed into the plasma 60. The monitor controller 94 provides command signals to the laser within the probe 92 to control its operation.

The monitor computer 96, which is normally a personal computer, is connected to the monitor controller 94 and functions to provide an input/output interface with the user and other devices. For example, the monitor computer 96 is connected to the sputter computer 38 through the sputter input/output interface 98. With prior systems, the particle sampling process is initiated simultaneously with the chamber power control 40 turning ON the D/C power supply 56. Thus, using the laser in the probe 92, the monitor controller 94 counts the number of particles detected during a sampling window. If, during any sampling period, the monitor controller counts a number of particles that exceeds a threshold number established by a laser in the monitor computer 96, the monitor computer commands either a visual or audio indicator (not shown) to turn ON. The monitor computer 96 may include statistical process control capabilities that permit the user to control when an alarm is turned ON. For example, the alarm may not be turned ON in response to only a single particle count exceeding the threshold, but instead, the user may require two or three or more consecutive particle counts in excess of the set point prior to turning the alarm ON. As will be appreciated, the statistical process control capability may be used in accordance with other methodologies. Further, the alarm signal may be activated by devices connected directly to the monitor computer 96. The alarm signal may also be passed to the sputter computer 38 via the sputter computer I/O interface 98, and the sputter computer 96 may activate other alarms and/or, under certain conditions, terminate the sputter coating process.

While that use of the particle monitor 90 is an improvement over counting processing kilowatt hours as a predictor for maintenance and cleaning, triggering the particle monitor operation with the power supply operation has certain disadvantages. The processing chamber 22 is not always in production when power is applied to the cathode assembly, for example, power may be applied to the cathode during maintenance and other non-production procedures. With the particle monitor operating during non-processing periods, memory in the monitor computer for storing the particle counts is unnecessarily used and wasted; and further, resetting and clearing particle alarms during nonproduction periods distracts personnel from other work.

Further, it was determined that the noise inherent in the plasma was interfering with, and inhibiting, the process monitor 90 from providing more accurate particle counts. With prior systems, the factory calibration of the particle monitor 90 is utilized during the monitoring process. However, if the particle monitor is calibrated in-situ in the processing chamber 22, it is believed that the effects of interference and noise from the gas plasma 60 can be minimized. In the normal execution or processing of a recipe, the sputter computer 38 commands the gas flow control 42 to initiate a flow of gas into the chamber a predetermined of time, for example, approximately ten seconds, prior to the sputter computer 38 commanding the chamber power control 40 to turn the D/C power supply ON. During that ten second period, before the power supply 56 is turned ON, the particle monitor 90 is recalibrated by the monitor computer 96 initiating the calibration process illustrated in FIG. 2.

Figure 2:
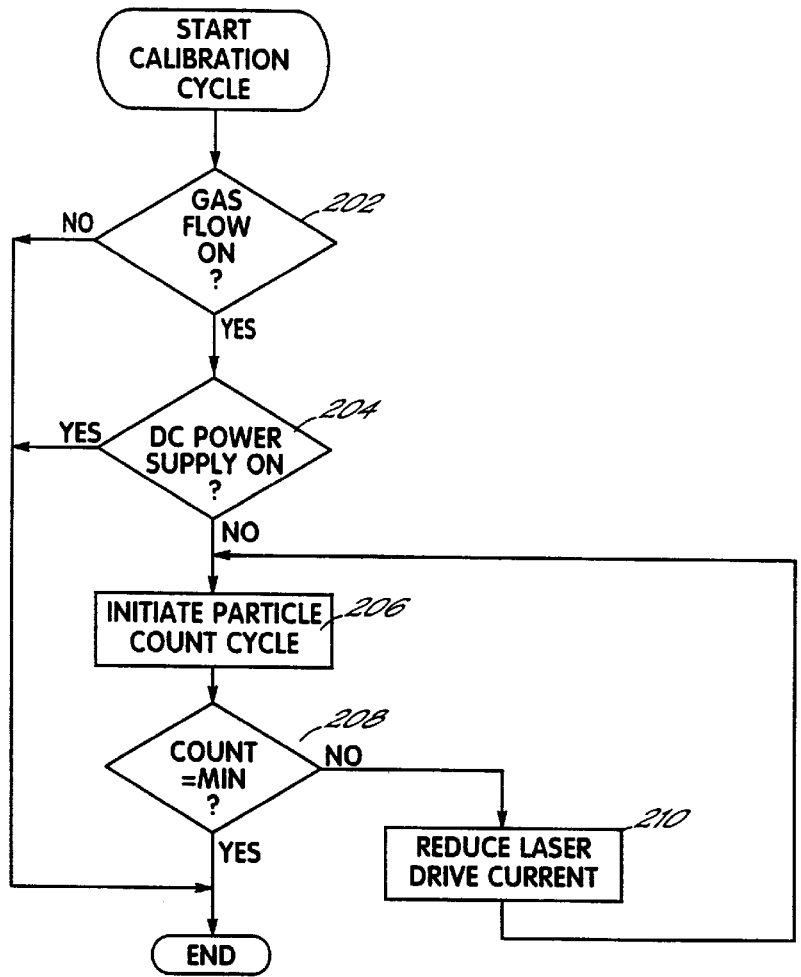
FIG. 2 is a flow chart of a subroutine of a calibration process executed by the particle monitor in accordance with the principles of the present invention.

The in-situ calibration process of FIG. 2 first detects, at 202, whether the gas is flowing into the chamber 22. Gas flow can be determined by detecting whether either the RG output solenoid 68 or the PG output solenoid 54 is in a state to open their respective output valves 72, 50. Alternatively, gas flow may be determined by detecting that both of the solenoids 54 and 68 are in a state to open the valves 72, 50. As a further alternative, the states of the input solenoids 52, 64, 74 may be either alone, in combination with each other, or in combination with the states of the output solenoids 54, 68. Signals relating to the states of the solenoids 54, 68 are provided from the gas flow control 42 to the monitor computer 96 over the line 100. Next, at 204, the process checks whether the power supply 56 is turned ON; and the state of the power supply 56 is provided from the chamber power control 40 to the monitor computer 96 over the line 102. Thus, if either the gas flow is OFF or the power supply 56 in ON, the calibration process ends.

If the gas flow is ON and the power supply 56 is OFF, to calibrate the monitor 90, the monitor computer 96 at 206 provides a command to cause the monitor controller 94 to initiate a particle count of the gases flowing in the processing chamber 22. If, at 208, more than a minimum particle count is detected by the monitor controller, it is assumed that the particle count is being caused by interference from the gases in the chamber 22. Therefore, the monitor computer 96 at 210 instructs the monitor controller 94 to reduce, by a predetermined amount or incremental magnitude, the magnitude of a current drive to the laser in the probe 92. The monitor computer 96 then at 206 initiates another particle count sample by the monitor controller 94. If particles are again detected, the monitor computer 96 commands a further reduction in the current drive to the laser. The process of steps 206–210 repeats until the monitor controller 94 has reduced the current drive to the laser in the probe 92 to a magnitude where the fewest or the minimal number of particles are detected at 208 during a particle sample time. The limitations of the capabilities of the particle monitor 90 and the harsh environment in which it operating practically limit the lower limit at which particles may be detected. However, the in-situ calibration process of FIG. 2 of the particle monitor 90 is effective to to eliminate particle counts caused by interference or noise created by the process gas flow through the processing chamber 22.

To further improve on the prior system and guarantee that the particle monitor 90 operates only when a wafer 26 is being coated by the sputter coating process, the particle monitor 90 is turned ON by a combination of signals. In one application of the sputter coating process, sputter coating of the wafer 26 only occurs when one or more of the reactive gases, for example, nitrogen and oxygen, flow into the processing chamber 22. Further, those gases will only flow into the chamber 22 when the reactive gas output valve 72 is open; and the valve 72 is opened only in response to energization of the reactive gas output solenoid 68 by the gas flow control 42. Therefore, upon the gas flow control 42 providing a signal to energize the reactive gas output solenoid 68, the gas flow control 42 simultaneously provides a signal on line 100 to the monitor computer 96 indicating that reactive gas is flowing into the processing chamber 22. Further, when the chamber power control 40 turns the DC power supply 56 ON, it simultaneously provides a signal on line 102 to the monitor computer 96. The monitor computer 96 combines those signals in a logical AND configuration, and hence, will initiate a particle sampling cycle only in response to receiving both signals, that is, the signal on line 100 from the gas flow control 42 indicating that the reactive gas is flowing into the chamber, and the signal on line 102 from the chamber power control 40 indicating that the D/C power supply is turned ON. Consequently, the process monitor 90 operates only when the processing chamber 22 is operating in production.

While the invention has been illustrated by the description of one embodiment and while the embodiment has been described in considerable detail, there is no intention to restrict nor in any way limit the scope of the appended claims to such detail. Additional advantages and modifications will readily appear to those who are skilled in the art. In the description with respect to FIG. 1, the operation of the particle monitor is started in response to initiating the flow of the first reactive gas, nitrogen, to the processing chamber. As will be appreciated, the operation of the particle monitor 90 can also be controlled by determining the flow of either of the reactive gases, nitrogen or oxygen or, a combination of the reactive gases or, the process gas or, a combination of one or more of the reactive gases and the process gas.

In the description of FIG. 1, upon the gas flow control 42 providing a signal to the RG gas output solenoid 68, a signal is simultaneously provided on line 100 to monitor computer 96. The signal provided to the RG gas output solenoid 68 is a binary signal with only two states. Thus, the signal on line 100 is similarly a binary signal with signal states that track the signal states of the signal operating the RG gas output gas solenoid 68. Alternatively, it may be desirable to provide a signal to the monitor computer 96 based on a signal from the gas flow control 42 operating one of the mass flow controllers 48, 66, 76. However, the signal provided by the gas flow control 42 to the mass flow controllers 48, 66, 76 is an analog signal, the amplitude of which sets the respective mass flow controller to the desired gas mass flow. Such an analog signal, having a wide range of amplitudes is unsuitable for use by the monitor computer 96 in a binary logic circuit. Therefore, to use the mass flow controller analog input signal, it must be converted to a corresponding binary digital signal utilizing an analog to digital converter.

Figure 3:
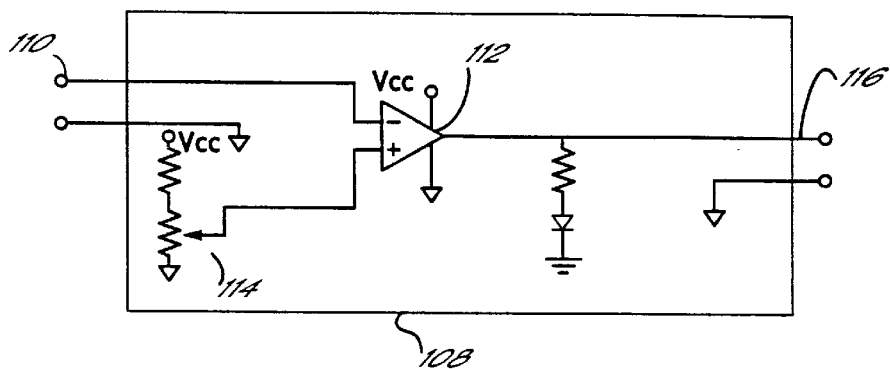
FIG. 3 is a detailed schematic diagram of an analog to digital converter that may be used in accordance with the principles of the present invention.

Referring to FIG. 3., an analog to digital converter 108 has an input 110 that receives from the gas flow control 42, an analog input signal corresponding to an input drive signal for a mass flow controller, for example, PG mass flow controller 48. The input 110 is connected to an operational amplifier 112. When the amplitude on the input 110 exceeds a predetermined set point or level, for example, 50 millivolts ("mv"), established by a variable resistor 114, the output 116 of the operational amplifier switches state, for example, from a ground level to the level of power supply voltage $V_{cc}$. When the mass flow controller input signal on 110 drops below 50 mv, the operational amplifier 112, switches its output 116 back to ground. Thus, the analog signal on input 110 is converted to a two state, binary signal on output 116. Normally, the 50 mv set point established by the variable resistor 114 represents the minimal value of the analog signal on the input 110 which of the mass flow controllers can discriminate. Further, the set point level established by the variable resistor 114 is adjustable by the user.

The above analog to digital converter is useful in those applications in which reactive gases are not used, and only the argon process gas flows into the chamber. While gas flow can be determined by detecting the state of the PG output solenoid, normally the process gas is turned ON and flows during the entire time a batch of wafers is being processed. However, at different times during that period, the deposition coating process may be interrupted while wafers are being transferred between stations and for other reasons. During those interruptions to the deposition process, the flow of gas is turned OFF using the mass flow controller 48. The particle monitor 90 should also be turned OFF during those interruptions to the deposition coating process. As described above, the analog to digital converter of FIG. 3 can be used to provide a binary signal to the monitor computer 96 in response to the analog input signal being provided by the gas flow control 42 to the PG mass flow controller 48.

The particle monitor in-situ calibration has been described with respect to a particle monitor sensor 92 mounted inside the processing chamber 22. However, as will be appreciated, the advantages of the in-situ calibration procedure are applicable to particle monitors that are located wholly outside the processing chamber 22. The particle monitor 90 has been described as operating with respect to a range of particle sizes, however, as will be appreciated, in the future, the range of particle size discrimination will increase with smaller size particles being detectable. The invention describe herein is applicable to other particle monitors that have different ranges of particle discrimination. Further, although the invention has been described as being applied to a PVD process, it is also applicable to other processes, for example, a chemical deposition process, whether low pressure, atmospheric pressure or plasma enhanced, an etching process, a diffusion process, etc.

Therefore, the invention in its broadest aspects is not limited to the specific details shown and described. Consequently, departures may be made from the details described herein without departing from the spirit and scope of the claims which follow.

What is claimed is:

1. A method of using a particle monitor control to initiate an operation of a particle monitor sensor detecting particles in a processing chamber, the method comprising the steps of:

providing a first signal to the particle monitor control in response to initiating a flow of gas to the processing chamber;

providing a second signal to the particle monitor control in response to the application of power to a cathode within the processing chamber; and initiating operation of the particle monitor by the particle monitor control only after the particle monitor control detects an occurrence of both of the first and the second signals.

2. A method of using a control system with a particle monitor control to initiate an operation of a particle monitor sensor detecting particles in a processing chamber, the method comprising the steps of:

initiating a flow of gas to the processing chamber with the control system;

providing a first signal from the control system to the particle monitor control in response to the control system initiating the flow of gas to the processing chamber;

initiating an application of power to a cathode within the processing chamber with the control system;

providing a second signal from the control system to the particle monitor control in response to the control system initiating the application of power to the cathode; and initiating operation of the particle monitor by the particle monitor control only after the particle monitor control detects an occurrence of both of the first and the second signals.

3. The method of claim 2 wherein the step of initiating a flow of gas further comprises initiating a flow of a process gas.

4. The method of claim 3 wherein the process gas is argon.

5. The method of claim 2 wherein the step of initiating a flow of gas further comprises initiating a flow of a reactive gas.

6. The method of claim 5 wherein the reactive gas is nitrogen.

7. The method of claim 5 wherein the reactive gas is oxygen.

8. The method of claim 2 wherein the step of initiating a flow of gas further comprises initiating a flow of a process gas and a reactive gas.

9. The method of claim 8 wherein the process gas is argon and the reactive gas is nitrogen.

10. The method of claim 2 wherein the step of initiating a flow of gas further comprises initiating a flow of a process gas and first and second reactive gases.

11. The method of claim 10 wherein the process gas is argon, the first reactive gas is nitrogen and the second reactive gas is oxygen.

* * * * *